United States Patent [19]

Hart

[11] Patent Number: 5,188,614

[45] Date of Patent: Feb. 23, 1993

[54] HYPODERMIC SYRINGE NEEDLE CONTAINMENT ASSEMBLY

[75] Inventor: Charles Hart, Laguna Beach, Calif.

[73] Assignee: Prac-Tech-Cal, Laguna Beach, Calif.

[21] Appl. No.: 680,347

[22] Filed: Apr. 4, 1991

[51] Int. Cl.⁵ .............................................. A61M 5/32
[52] U.S. Cl. .................................. 604/197; 604/198; 604/110; 128/919
[58] Field of Search ........ 604/110, 111, 192, 194–198, 604/263, 187, 218; 128/919

[56] References Cited

U.S. PATENT DOCUMENTS

| | | | |
|---|---|---|---|
| 4,692,156 | 9/1987 | Haller | 604/195 |
| 4,767,413 | 8/1988 | Haber et al. | 604/198 |
| 4,887,998 | 12/1989 | Martin et al. | 604/110 |
| 4,917,673 | 4/1990 | Coplin | 604/198 |
| 4,927,414 | 5/1990 | Kulli | 604/110 |
| 4,927,416 | 5/1990 | Tomkiel | 604/198 |
| 4,927,417 | 5/1990 | Moncada et al. | 604/198 |
| 4,929,237 | 5/1990 | Medway | 604/198 |
| 4,932,939 | 6/1990 | Magre et al. | 604/110 |
| 4,932,940 | 6/1990 | Walker et al. | 604/110 |
| 4,932,941 | 6/1990 | Min et al. | 604/110 |
| 4,932,947 | 6/1990 | Cardwell | 604/198 |
| 4,966,592 | 10/1990 | Burns et al. | 604/198 |
| 4,986,819 | 1/1991 | Sobel | 604/198 |
| 5,013,301 | 5/1991 | Marotta et al. | 604/197 |
| 5,013,302 | 5/1991 | Schmidt | 604/198 |
| 5,088,986 | 2/1992 | Nusbaum | 604/195 |
| 5,122,118 | 6/1992 | Haber et al. | 604/110 |

Primary Examiner—John D. Yasko
Assistant Examiner—Mark O. Polutta
Attorney, Agent, or Firm—Lyon & Lyon

[57] ABSTRACT

A protective device for use with a hypodermic syringe for preventing accidental needle sticks after fluid has been ejected from the syringe and rendering the syringe non-reuseable. The protective device comprises a hollow, cylindrical casing defining a forward end wall having an opening therein, a rearward open end and an angular gripping flange adjacent the rearward end. The casing is adapted to be disposed about the syringe such that the syringe is reciprocally translatable therein with the syringe needle projecting through the opening in the forward end wall of the casing and the angular gripping flange axially spaced from the syringe flange. A dual component foaming agent is disposed in the casing adjacent the forward end wall thereof which, when the components thereof are mixed together activate to form an expanding and hardening plastic foam. Collapsible tabs are carried by the casing for spacing the syringe from the foaming agent prior to and during ejection of fluid from the syringe to prevent inadvertent activation of the foaming agents. Upon pressing the syringe into the casing subsequent to the ejection of fluid from the syringe, the foaming agents are activated and the expanding foam forces the syringe and syringe needle rearwardly within the casing and passes about the needle and through the forward end of the casing and hardens, thereby encapsulating the used needle within the casing and foam.

32 Claims, 5 Drawing Sheets

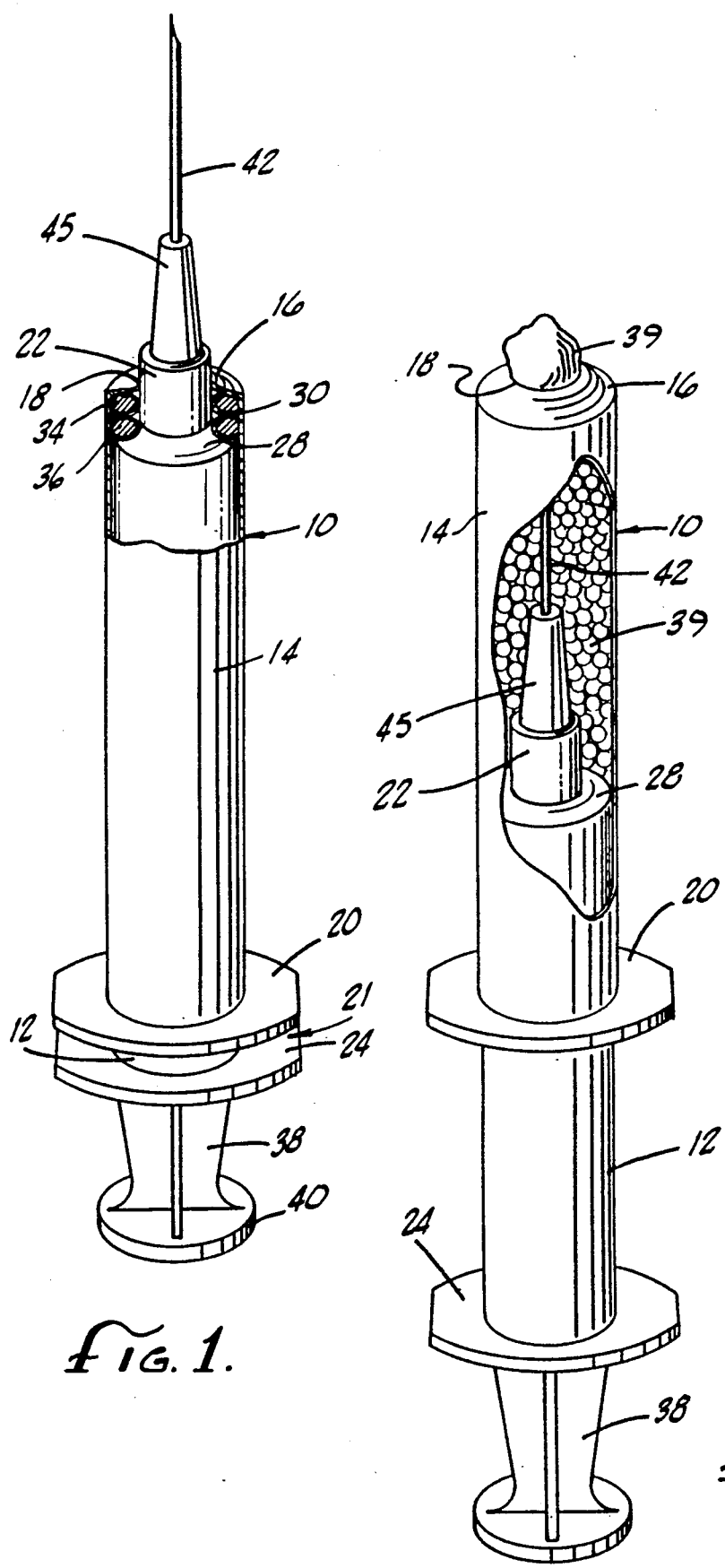

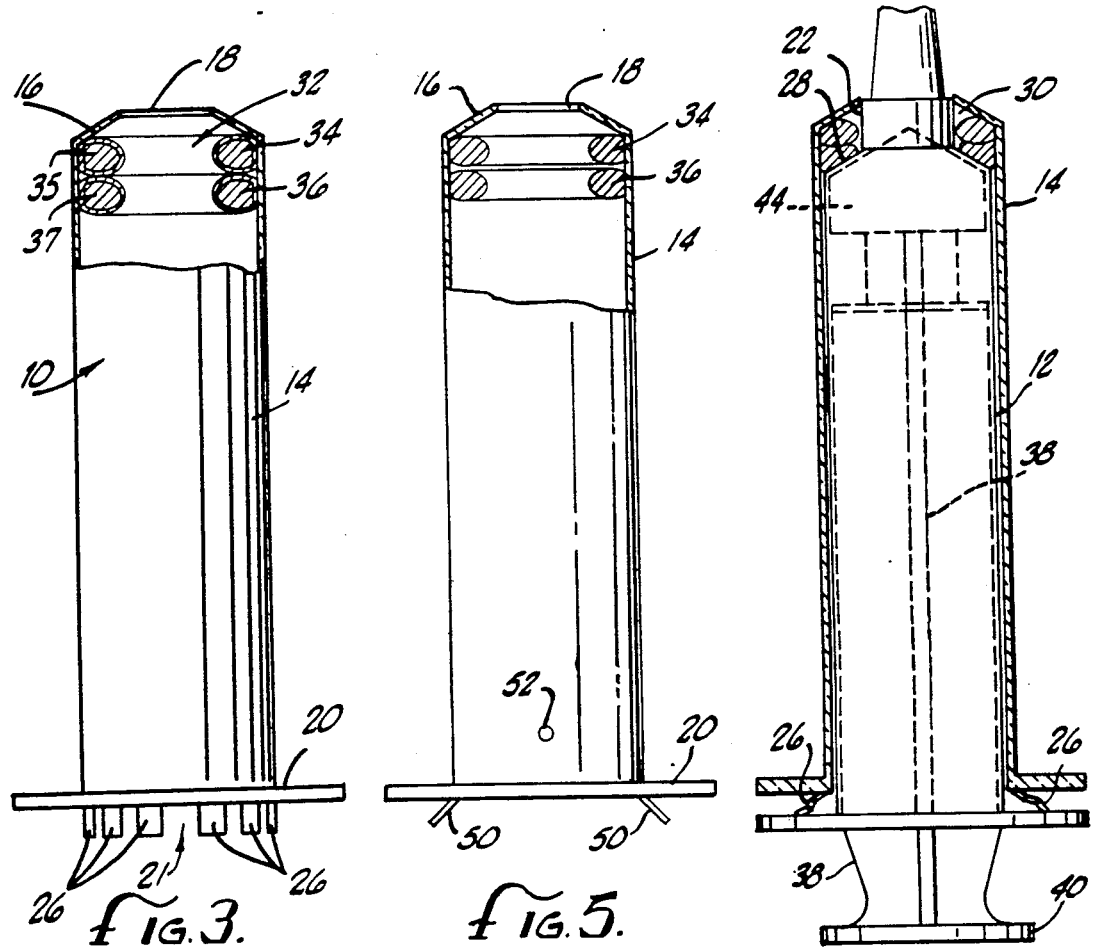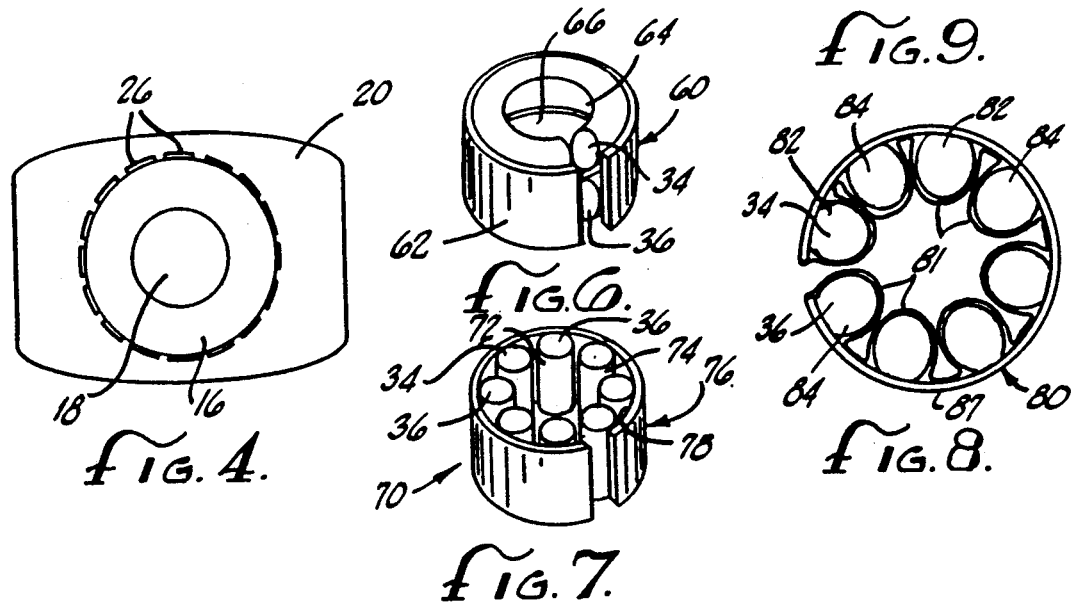

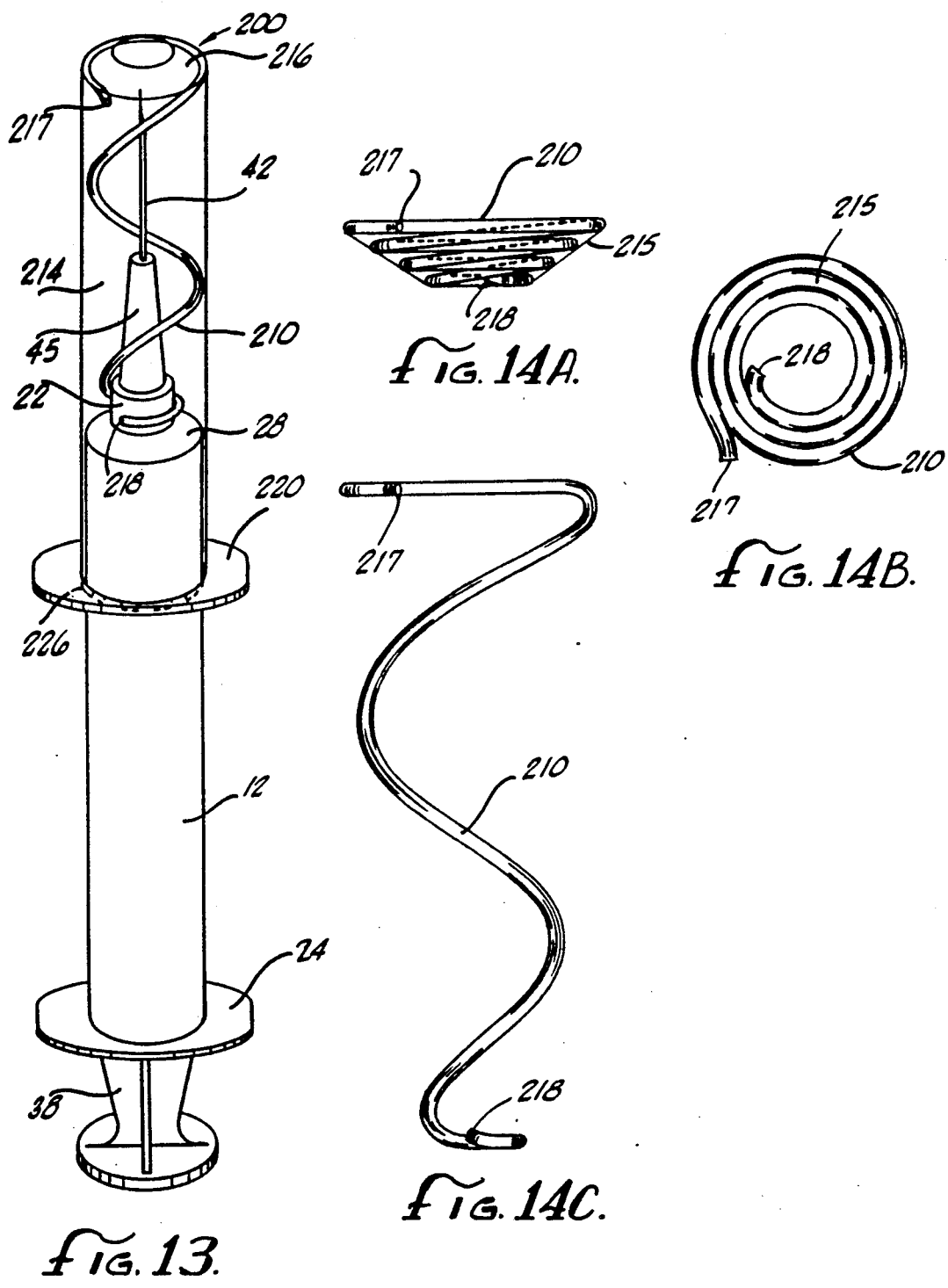

HYPODERMIC SYRINGE NEEDLE CONTAINMENT ASSEMBLY

BACKGROUND OF THE INVENTION

The present invention relates to a containment device for use with medical syringes which provides protection against accidental needle sticks and renders the syringe non-reusable It is well known that several contagious and very dangerous diseases, such as hepatitis and acquired immune deficiency (AIDS), are readily transmitted by contact with residual body fluids found on or within a used medical syringe or needle. For this reason as well as to inhibit drug abuse, most syringes are currently intended for single use. The safe handling of single-use syringes by the user, and those who must dispose of the used syringes, is a matter of urgent concern. In most cases, a protective cap is provided for protection prior to use. However, it is after the needle is used that it is most dangerous. The Center for Disease Control has issued a guide line stating that it is recommended that health- care workers not attempt to replace safety caps after injection due to the fact that many needle sticks occur as a result of this procedure, which may result in exposure to blood-born diseases or other organisms or infections that might be present on a used needle.

There have been many attempts to resolve the problem of accidental needle sticks and unauthorized reuse of syringes and needles. Most of these efforts focused on attempts to effect retraction of the used needle to a position within the syringe or an extension thereof, the placement of a protective sleeve about the needle, or the placement of the syringe and/or needle into a safe container. These attempts, however, have not provided an acceptable solution to the problem. To prevent both accidental needle sticks and unauthorized reuse, a solution should preferably include the following: a mechanism which automatically retracts the needle assembly into a protected environment; a mechanism that is compatible with most existing syringes and needles; a mechanism which if used in combination with existing syringes does not change the capacity or tactile features of the syringe or interfere in any way with the use of the syringe and needle; a device which requires only one-handed operation; a device which would not only retract the needle assembly into a protected environment but also encapsulate and isolate the contaminated needle; a device which would indicate the presence of a contaminated needle; a device, the cost of which would be sufficiently small as to present little or no negative economic reaction; a device of simple construction having a minimum of moving parts and which is readily manufacturable. The protective device of the present invention provides each of these features.

SUMMARY OF THE INVENTION

Briefly, the protective device of the present invention comprises a transparent cylindrical casing having an opening in the forward end thereof and an annular gripping flange adjacent the rearward open end thereof. The casing is adapted to be dispersed about the barrel of a conventional syringe and is sized such that the syringe needle, needle connector and hub project through the aperture in the forward end of the casing, the annular gripping flange is spaced a short distance from the syringe flange and the distal end of the syringe barrel spaced is from the forward end of the casing. A two-component expandable foaming means is disposed within the casing adjacent the forward end thereof. Collapsible detention means extend between the casing of the protective device and the syringe which maintain the spacing between the gripping flange on the protective device and the syringe flange and thus prevent the distal end of the syringe from being driven into and mixing the two components of the foaming means prior to and during normal use of the syringe.

Upon completing the injection and applying additional force to the syringe plunger, the detention means collapses, allowing the distal end of the syringe to compress the two components of the foaming means against the end wall of the casing, mixing the components together and effecting a chemical reaction creating a rapidly expanding plastic foam. The expanding foam forces the syringe and needle rearwardly within the casing, passes about the needle and through the opening forward end of the casing and quickly hardens, thereby encapsulating the used needle within the casing and foam, permanently fixing the syringe in a retracted position within the casing, and providing visible evidence of the presence of a contaminated needle.

It is the principal object of the present invention to provide an improved safety protective device for use with a hypodermic syringe which substantially reduces the occurrences of needle sticks after injection and renders the syringe nonreusable.

It is another object of the present invention to provide an improved safety containment device for use with a hypodermic syringe which provides automatic retraction of the syringe and attached needle to a position within the safety containment device subsequent to full discharge of the fluid held within the included syringe.

It is yet another object of the present invention to provide an improved safety containment device for use with a hypodermic syringe in which automatic retraction, complete encapsulation, water-proof isolation and identification of a used hypodermic syringe needle is provided.

It is yet another object of the present invention to provide an improvement in a safety containment device for use with a hypodermic syringe which prevents the reuse of the hypodermic syringe by automatically retracting and permanently encapsulating the syringe needle after a single use thereof, whereby the syringe and needle are rendered non-reusable.

It is a still further object of the present invention to provide an improved safety containment device for use with hypodermic syringes which does not alter the operation or feel of the syringe during use.

These and other objects and advantages of the present invention will become readily apparent from the following detailed description taken in conjunction with the accompanying drawings. Insofar as these objects and advantages are within the purview of the appended claims, they are to be considered as part of the present invention.

IN THE DRAWINGS

FIG. 1 is a perspective view of the protective device of the present invention shown disposed on a medical syringe prior to use with a portion of the outer wall of the device broken away to illustrate the foaming means therein.

FIG. 2 is a perspective view of the protective device of the present invention shown disposed on a medical syringe after use with a portion of the device broken away to illustrate the encapsulation of the syringe needle by the protective foam.

FIG. 3 is a sectional view of the casing of the present invention.

FIG. 4 is a bottom view of the casing of the present invention.

FIG. 5 is a sectional view of the protective device of the present invention illustrating alternative detention means for preventing inadvertent activation of the foaming means.

FIG. 6 is a perspective view of a first alternate embodiment of the foaming means of the present invention wherein the two reactive components thereof are disposed within a flexible container ring.

FIG. 7 is a perspective view of a second alternative embodiment of the foaming means of the present invention wherein the two reactive components thereof are formed into a plurality of vertically disposed cylinders carried by and within a flexible container ring.

FIG. 8 is a top view of a modified form of the foaming means shown in FIG. 7 wherein a membrane is used to isolate the reactive components in the foaming means.

FIG. 9 is a sectional view of the protective device of the present invention showing relative positioning of the syringe and syringe plunger therein when the foaming means has been compressed between the distal end wall of the syringe and the forward end wall of the casing after the syringe plunger has fully discharged the fluid within the syringe.

FIG. 13 is a perspective view of an alternate embodiment of the present invention wherein the syringe/needle retraction mechanism comprises a sealed coiled spring.

FIG. 14A is a side view of the activating spring of the alternate embodiment of the invention in a semi-compressed condition.

FIG. 14B is a top view of the activating spring of the alternate embodiment of the invention in a semi-compressed condition.

FIG. 14C is a perspective view of the activating spring of the alternate embodiment of the invention in its extended condition.

DESCRIPTION OF THE PREFERRED EMBODIMENTS

Figure 10A:
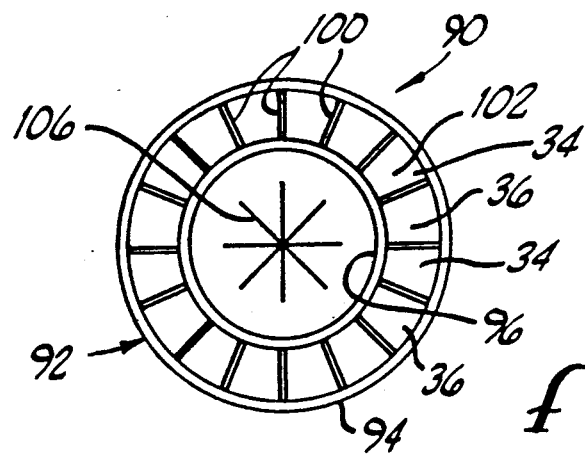
FIGS. 10A-10D illustrate a third alternative embodiment of the foaming means of the present invention.
Figure 10B:
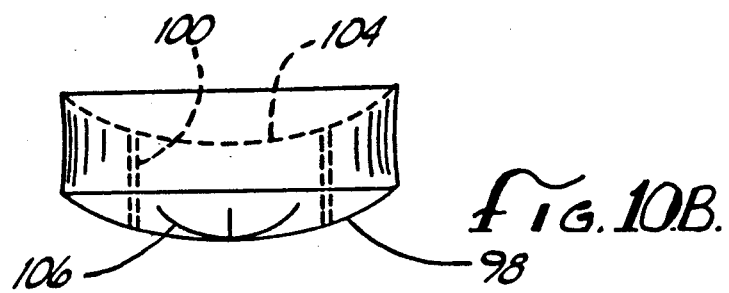
Figure 10C:
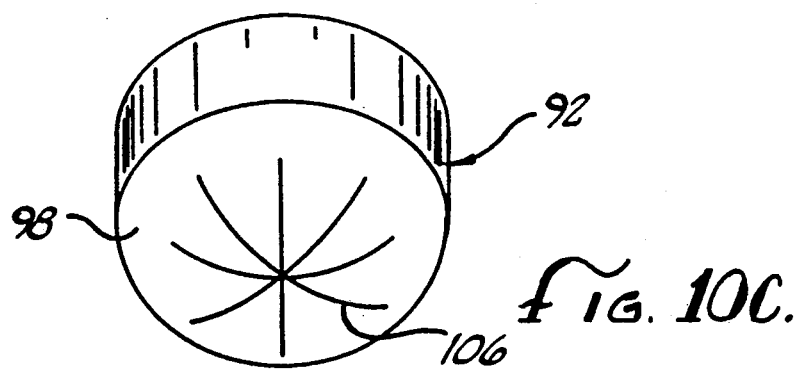
Figure 10D:
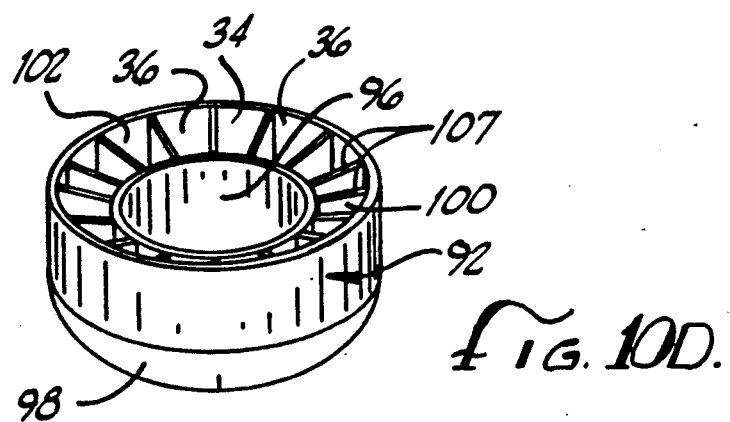

The protective device 10 of the present invention is adapted to be disposed about the barrel of a conventional disposable syringe 12, as seen in FIG. 1. The protective device 10 (shown separately in FIG. 3) comprises a hollow cylindrical casing 14 having a forward end wall 16, which defines a central opening 18 therein, and an annular gripping flange 20 disposed adjacent the rearward open end 21 thereof. Opening 18 is sized so as to provide a close fit about the hub 22 of syringe 12. Annular flange 20 is of the same configuration and size as the standard flange 24 on a conventional syringe 12 and is spaced therefrom by a plurality of collapsible or breakable thin plastic detention tabs 26 which project rearwardly from the underside of flange 2 about the open end 21 of syringe 12 as seen in FIGS. 3 and 4. Casing 14 is preferably constructed of a clear plastic material so that the gradient markings on the syringe may be read therethrough and flange 20 and tabs 26 are preferably formed therewith. Casing 14 is sized such that the syringe 1 is reciprocally translatable therein and when tabs 26 abut syringe flange 24, the forward end wall 16 of the casing is spaced from the distal end 28 of the syringe to provide a spacing 30 therebetween.

A dual component, chemically reactive, expandable foaming means 32 is disposed in the forward end of casing 14 adjacent end wall 16 thereof, such that when the protective device 10 is disposed over syringe 12, the foaming means 32 is disposed in the spacing 30 between the end wall 16 of casing 14 and the distal end 28 of syringe 12, as seen in FIG. 1. In the preferred embodiment of the invention, foaming means 32 is a two-component thermosetting polymer with one of the components 34 comprising isocyanate and the other components comprising polyol (polymer resin) with a blowing agent of either fluorocarbon or water being added thereto. In the embodiment of the invention illustrated in FIGS. 1 and 3, the two components 34 and 36 are separately and sequentially deposited in the form of highly viscus pastes into two vertically aligned toroids 35 and 37 in the distal end of casing 14 adjacent end wall 16 thereof.

The nature of the two components 34 and 36 of foaming means 32 are such that they cannot be disposed in contact with oneanother without reacting. Accordingly, as seen in FIGS. 1 and 3, a thin protective membrane 41 is disposed about the toroids of reactive components 34 and 36 to prevent inadvertent contact and premature mixing thereof. Such a membrane could be formed of tin foil, a thermoplastic or other suitable material which could be easily penetrated by the distal end of the syringe to press the two foaming components together to effect mixing and activation thereof. Alternatively, the protective membrane could be disposed about just one of the components 34 or 36 to prevent such mixing.

FIG. 5 illustrates an alternate embodiment wherein the two reactive components 34 and 36 are spaced axially apart and a protective membrane is not employed. The tacky outer surfaces of the two components will hold the deposited toroids thereof in place against the interior surface of casing 14. Care must be taken in depositing the components without the use of a protective membrane to avoid contact thereof and premature mixing of the components.

Figure 12:
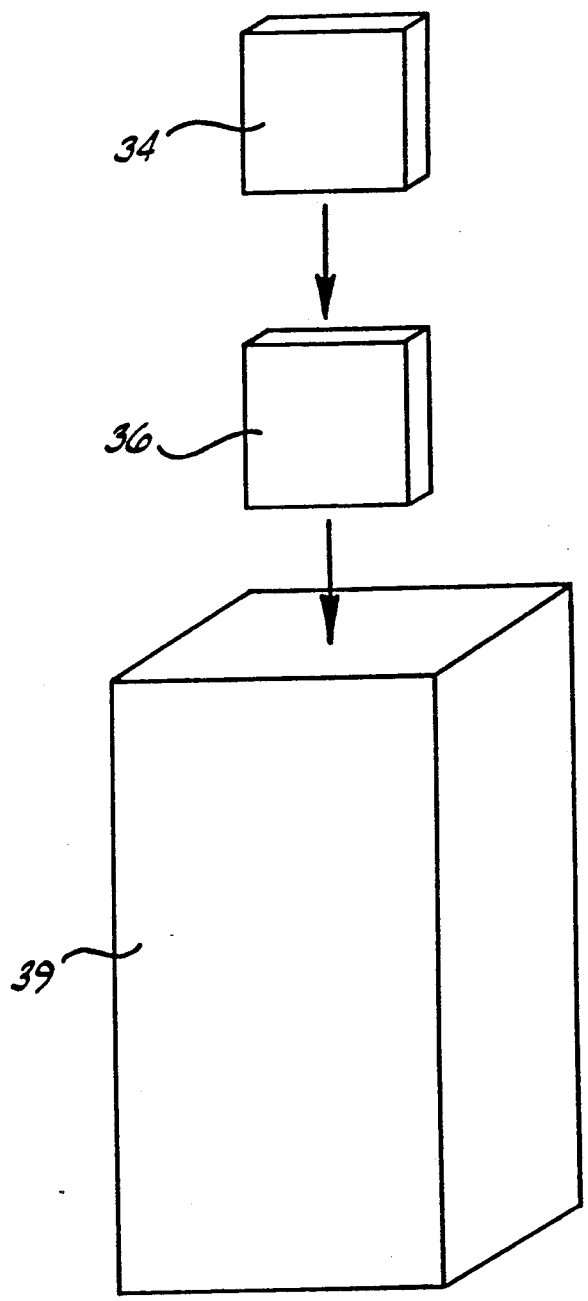
FIG. 12 depicts the chemical process of the foaming means upon activation thereof, illustrating the volumetric proportions of the two components prior to and after mixing.

When the two reactive components 34 and 36 are pressed together, they mix and quickly react to produce a rapidly expanding plastic foam 39 which quickly hardens into a rigid, substantially closed cell configuration. The volumetric expansion of reactive components 34 and 36 into foam 39 is schematically illustrated in FIG. 12. Tabs 26 maintain a minimum spacing between the annular gripping flange 20 on casing 14 and syringe flange 24 and thus prevent the intrusion of the distal end 28 of the syringe into foaming means 32 which would result in a mixing of components 34 and 36 and actuation of the aforesaid reaction.

In use, the protective device 10 is disposed over the syringe barrel such that the collapsible tabs 26 abut the syringe flange 24 and the syringe hub 22 projects through the opening 18 in the end wall 16 of casing 14 as seen in FIG. 1. The syringe plunger 38 is then operated in a conventional manner to load the syringe with an appropriate fluid by gripping the end flange 40 thereon and syringe flange 24 to effect withdrawal of the plunger 38 within the syringe barrel and thus aspirate fluid into the syringe barrel through needle 42. The fluid is then dispensed from the syringe in the conventional manner except that the syringe is held by the casing 14 of the protective device 10 and the annular gripping flange 20 thereon. By configuring annular flange 20 in the same manner as the syringe flange 24 and disposing flange 20 substantially adjacent flange 24, the user experiences substantially the same "feel" in handling the device while giving an injection as one would with a conventional syringe not employing the protective device 10.

When the discharge of the fluid from the syringe is complete, the piston 44 at the forward end of the syringe plunger 38 reaches the distal end 28 of the syringe. Continued pressure upon the plunger 38 transfers the force of such pressure through the plunger to the barrel of the syringe with sufficient strength to deform, bend, break or otherwise collapse the detention tabs 26 between flanges 20 and 24. With the collapse of the detention tabs 26, the syringe 12 moves forward within casing 14, whereupon the distal end syringe compresses the reactive components 34 and 36 of the foaming means 32 against the end wall 16 of casing 14 which deforms the adjacent toroids 35 and 37, fracturing any protective membranes 41 therebetween and thus effects a mixing of the two reactive components 34 and 36. Within a few seconds of such mixing, the resultant chemical reaction produces a plastic foam which expands, pressurizing the area between the distal end 28 of the syringe 12 and the end wall 16 of casing 14 and forcing the syringe 12, needle 42 and needle holder 45 into a withdrawn or retracted position within casing 14 as seen in FIG. 2. Concurrently, the resultant foam passes about syringe needle holder 45 and needle 42 and through the opening 18 in the end wall 16 of casing 14. In about 20 seconds, the resultant foam hardens into a rigid substantially closed cell plastic foam having a water impermeable skin, a density of between 1.5-2.5 pounds per square inch and a compression strength of about 30 psi so as to prevent re-extension of the syringe needle 42 through opening 18 and provide complete encapsulation and isolation of the contaminated needle 42 within casing 14.

By increasing the proportion of dicarboxylic acid to glycol in the polyol component 36 of foaming means 32 the resultant foam has strong adhesive properties such that the forward portion of syringe 12, needle 42 and needle holder 45 are secured within casing 14, effecting permanent containment encapsulation and isolation of the contaminated needle 42. As the resultant foam is approximately 90% closed cell configuration an excellent seal around the encapsulated needle 42 is provided and the opening 18 in casing 14 is effectively sealed, thereby forming an effective device for the safe handling of contaminated needles and syringes. If desired, the reactive component, 34 and 36 could be pigmented with a bright color so that the resultant foam 39, which can be seen both through the transparent syringe barrel and casing 14 and which protrudes through the opening 18 in the casing 16, provides graphic indication of the presence of a used needle.

In the above description of protective device 10, collapsible tabs 26 provide a detention means in maintaining the necessary separation between gripping flange 20 on casing 14 and the syringe flange 24 to prevent premature inadvertent activation of the foaming means 32. Tabs 26, can be configured in a wide variety of ways so as to deform, bend, break or otherwise collapse upon the application of the desired pressure against the syringe plunger 38 to effect activation of the foaming means 32. Other means of holding the protective device 10 and syringe 12 in the desired spacial relationship could also be employed. By way of example, two alternate embodiments of such means are illustrated in FIG. 5. In lieu of a plurality of collapsible tabs 26 disposed about the perimeter of the open end 21 of casing 14, as seen in FIG. 3, the annular flange 20 on casing 14 could carry a pair of transversely disposed inclined tabs 50 which deflect under the application of force against plunger 38. Alternatively, a heat pierced temporary weld 52 extending through the casing 14 to the syringe barrel could be employed which would break upon pressing firmly against the plunger 38 after the fluid within the syringe had been ejected, allowing the syringe to move forwardly into foaming mean 32 and effect mixing of the reactive components. The term collapse is used herein to mean and include any form of bending, breaking, deforming, separation, etc. or the detention means.

FIGS. 6-8 are illustrative of alternate configurations of the foaming means which could be employed in the protective device 10 of the present invention. While the two component thermal setting polymer employed in the foaming means 32 remains unchanged in these alternate embodiments, the configuration of and the method of deploying the two reactive components 34 and 36 in the casing 14 can be varied.

FIG. 6 illustrates a foaming means 60 in which the two reactive components 34 and 36 are deposited within a split container ring 62 in the form of two split vertically aligned toroids 64 and 66. Ring 62 is preferably constructed of a flexible thin plastic material and defines an outer diameter slightly larger than the inner diameter of casing 14, allowing the ring container 62 and split toroids of the reactive components foaming agents contained therein to be compressed slightly and slided axially within casing 14 to the forward end wall 16 thereof, whereupon the resilient nature of ring 62 will cause the compressed ring to flex outwardly against the interior surface of the casing, holding the foaming means 60 in place.

The foaming means 70 of FIG. 7 is similar to foaming means 60 except that the two reactive components 34 and 36 are formed into a plurality of cylinders 72 and 74 which are alternately aligned in an axial disposition within and against the containing ring 76, as seen in FIG. 7. As the external surfaces of the two reactive components 34 and 36 are quite tacky, the cylinders 72 and 74 will readily adhere to the interior side wall 78 of ring 76.

The foaming means 80, illustrated in FIG. 8, is similar to foaming means 70 of FIG. 7, except that a thin membrane 81 of tin foil, thermoplastic or other suitable material is disposed about the external surfaces of the formed cylinders 82 and 84 of reactive components 34 and 36 to form a protective barrier about the reactive components which may prove useful in prolonging the shelf line of the foaming means. Membrane 81, is, however, sufficiently thin so as not to adversely effect the mixing of the two components when compressed within ring 87 between the distal end 28 of the syringe 12 and the end wall 16 of casing 14 as previously described.

Yet another embodiment of the foaming means is illustrated in FIGS. 10A-10D. This embodiment is particularly designed for use with reactive components 34 and 36 being formed in a liquid state as opposed to the highly viscus paste composition employed in the toroidal and cylindrical configurations of the preceding embodiments. Foaming means 90 comprises a thin walled readily deformable cup member 92 which is preferably constructed of a material such as latex, vinyl or polypropelene. Cup member 92 defines an outer cylindrical wall 94 having a diameter corresponding to the internal diameter of casing 14, an inner wall 96 having a diameter corresponding to the outer diameter of syringe hub 22, a dome-shaped upper wall 98 (shown inverted in FIGS. 10A-10D) adapted to be disposed adjacent end wall 16 of casing 14, and a plurality of radial walls 100 extending between cup walls 94, 96 and 98 so as to define an even number of separate cells 102. The two reactive components 34 and 36 are then alternately deposited in cells 102 and a thin membrane covering 104 is disposed about the underside of cup member 92 to seal the cells and prevent leakage of the reactive components therefrom. Membrane 104 could be constructed of tin foil or a thermoplastic material sprayed or otherwise disposed over the lower surface of the cup member. The dome-shaped upper wall of the foaming means 90 is preferably provided with scores 106 therein to provide easy penetration of the syringe needle 42, holder 45 and syringe hub 22 therethrough. The outer wall 94 of cup member 92 extends below inner wall 96 so that the lower surfaces 107 of radial walls 100 are inclined from the outer wall 94 to the inner wall 96 so as to define a centering means for the passage of the needle holder 45 and syringe hub 22 through the cup member 92.

The foaming means 90 is positioned in the forward end of casing 14 with the dome-shaped upper wall 98 being disposed adjacent the end wall 16 of casing 14. Upon inserting the casing 14 over the syringe 12, the needle 42 will puncture the upper wall 98 of foaming means 90 allowing the needle, needle holder and syringe hub to pass therethrough and through opening 18 in the end wall 16 of casing 14. Upon ejecting all of the fluid within the syringe barrel through needle 42, the application of sufficient force on plunger 38 to deform detention tabs 26 causes the distal end 28 of the syringe to pass through the lower membrane 104 on foaming means 90 and destruct cells 102, allowing the reactive components 34 and 36 contained therein to mix together and chemically react and effect withdrawal of the syringe 12 and needle 42 into casing 14 and encapsulate the needle therein as previously described.

Figure 11:
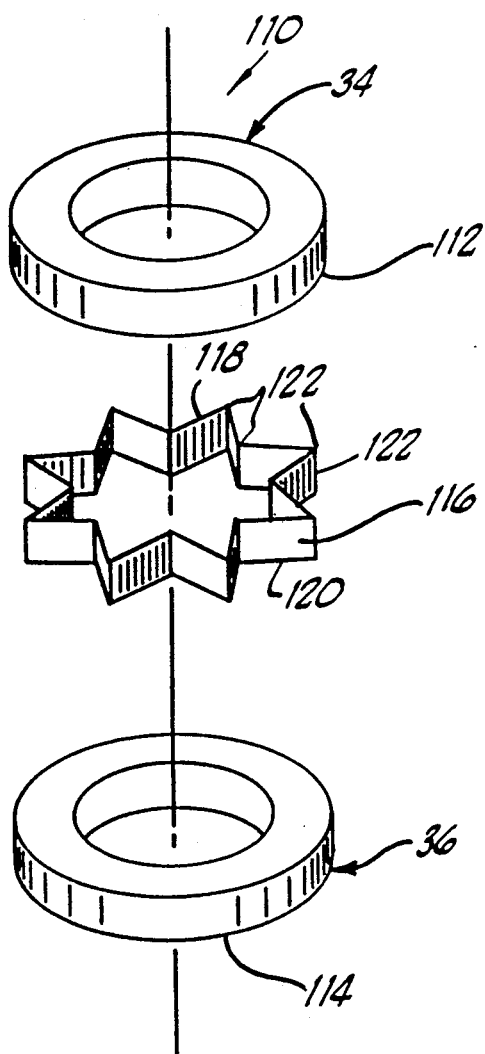
FIG. 11 is an exploded view of a fourth alternative embodiment of the foaming means of the present invention wherein the two reactive components are formed into horizontally disposed toroids separated by a cutting and mixing member.

FIG. 11 is illustrative of yet another embodiment of a foaming means 110 for use with the present invention wherein the two reactive components 34 and 36 are formed into toroids 112 and 114 and a cutting and mixing element 116 is disposed therebetween. Element 116 can be constructed of thin plastic or other suitable material and is configured so as to define upper and lower cutting edges 118 and 120. To maximize the interface created by these cutting edges, element 116 defines a plurality of bends 122 therein. The toroids 112 and 114 of reactive components 34 and 36 which are axially aligned adjacent cutting element 116, as represented in FIG. 11, are sized so as to define an outer diameter substantially the same as the inner diameter of casing 14 so as to be held in place adjacent end wall 16 thereof by the frictional force they exert against the interior wall of casing 14. When the two toroids are pressed against the cutting edges 118 and 120 of element 116 by the distal end 28 of the syringe 12 following expulsion of the fluid from the syringe, the toroids of reactive components are severed along the cutting edges 118 and 120 and effectively mixed together by the compressive force exerted thereon by the syringe to activate the foaming reaction.

An alternate embodiment of a syringe protection device 200 is illustrated in FIGS. 13 and 14. This embodiment differs from the prior embodiments in that the foaming means of the prior embodiments is replaced with a coil spring 210 which is disposed within casing 214 about syringe hub 22 and is extendable to a length sufficient to provide retraction of the syringe 12 and attached needle 42 to a position within casing 214. Casing 214 is identical to casing 14 of the prior embodiment and includes the same annular gripping flange 220 and detention tabs 226. The extended end 217 of the outermost concentric winding of spring 210 defines a tight bend in an outward direction to provide frictional resistance to movement of the spring within casing 214. The innermost end 218 of spring 210 defines a tight inward bend toward the center of spring 210 which bears against syringe hub 22 providing resistance to the withdrawal of the hub from spring 210. Spring 210 is coated while in the semi-compressed condition illustrated in FIGS. 14A and 14B with a fracturable coating of a thermoplastic, epoxy, polyester, acrylic, glass or other readily fracturable material 215 which will retain the spring 210 in its semi-compressed condition until sufficient pressure is applied to the spring to fracture the coating, allowing the spring 210 to expand within casing 214 to the extended position illustrated in FIGS. 13 and 14C. Under normal use in administering an injection, the spring 210 is not subjected to any disruptive force which would fracture the confining coating 215, as the collapsible tabs 226 on the underside of annular flange 220 prevent the distal end 28 of the syringe 12 on which spring 210 is disposed from compressing the spring against forward end wall 216 of casing 214 which would fracture coating 215. However, when sufficient force is applied to the syringe plunger 38 so as to collapse tabs 226, the distal end 28 of the syringe presses the semi-compressed spring 210 against the end wall 216 of casing 214, fracturing the confining coating 215 on the spring and allowing the spring rapidly to expand to its extended position. As spring 210 expands, it forces the syringe and needle rearwardly within casing 214, as shown in FIG. 13, protecting one from an inadvertent needle stick. This alternate embodiment does not permanently disable the syringe and is thus adaptable for use with a reusable syringe wherein the spring member 210 is the only component which must be replaced.

These and other modifications may be made in carrying out the present invention without departing from the spirit and scope thereof. Insofar as these changes and modifications are within purview of the appended claims, they are to be considered as part of the present invention.

I claim:

1. A protective device for use with a hypodermic syringe for preventing accidental needle sticks after fluid has been ejected from the syringe, said device comprising:

a hollow cylindrical casing defining a forward end wall having an opening therein, a rearward open end and an annular gripping flange adjacent said rearward end, said casing being adapted to be disposed about a syringe such that the syringe is reciprocally translatable therein, the syringe needle projects through said opening in said forward end wall and said gripping flange is axially spaced from the syringe flange;

exandable means disposed in said casing adjacently said forward end wall thereof, said means being activated to an expanded state upon being compressed adjacent said forward end wall of said casing; and collapsible means carried by said casing and being adapted to abut the syringe upon said casing being disposed about the syringe to prevent the syringe from compressing said expandable means prior to and during ejection of fluid from the syringe and collapsing upon the application of additional force being exerted upon the syringe subsequent to such ejection, allowing the syringe to compress and activate said expandable means, whereupon said expandable means expands within said casing adjacent the forward end wall thereof to force the syringe rearwardly within said casing and draw the syringe needle into said casing.

2. The protective device of claim 1 wherein said collapsible means comprises a plurality of collapsible tab members projecting rearwardly from said angular gripping flange and abutting the syringe flange upon said casing being disposed about the syringe.

3. The protective devices of claims 1 or 2 wherein said expandable means comprises a spring member and fracturable means disposed about spring member for maintaining said spring member in a semi-compressed state within said casing prior to and during the ejection of fluid from the syringe, said fracturable means being adapted to be fractured upon the syringe pressing said fracturable means against the end wall of said casing so as to release said spring member whereupon said spring member expands, forcing the syringe and the syringe needle rearwardly within said casing.

4. The protective devices of claim 3 wherein said spring member defines a coil spring, the outer end thereof bearing against the interior of said casing proximate said end wall thereof and the inner end of said spring member being adapted to abut and bear against the syringe.

5. The protective devices of claim 3 wherein said fracturable means comprises a thermoplastic epoxy, polyester or acrylic coating disposed about said spring member.

6. The protective devises of claim 3 wherein said fracturable means is glass.

7. A protective device for use with a hypodermic syringe for preventing accidental needle sticks after fluid has been ejected from the syringe, said device comprising;

a hollow cylindrical casing defining a forward end wall having an opening therein, a rearward open end and an annular gripping flange adjacent said rearward end, said casing being adapted to be disposed about a syringe such that the syringe is reciprocally translatable therein, the syringe needle projects through said opening in said forward end wall and said gripping flange is axially spaced from the syringe flange;

exapandable means comprising a two-component foaming means, the two components of said means being spaced apart within said casing; and collapsible means carried by said casing and being adapted to abut the syringe upon said casing being disposed about the syringe to prevent the syringe from compressing said expandable means prior to and during ejection of fluid from the syringe and collapsing upon the application of additional force being asserted upon the syringe subsequent to such ejection, allowing the syringe to compress and activate said expandable means whereby upon being compressed within said casing upon the collapse of said collapsible means, the two components of said foaming means mix together and react to form an expanding foam for forcing the syringe rearwardly within said casing and harding about the syringe needle therein to encapsulate the needle within the hardened foam in said casing.

8. The protective devices of claim 7 wherein said casing is formed of a transparent plastic material.

9. The protective devices of claim 7 wherein one of said components is comprised of isocyanate and the other of said components is comprised of polyol.

10. The protective devices of claim 7 wherein said components are deposited within said casing so as to define a pair of toroids, a first toroid comprising one of said components and being disposed adjacent said end wall of said casing the second of said toroids comprising the other of said components and being spaced axially from said first toroid to prevent premature mixing of said components prior to compression thereof by the syringe.

11. The protective devices of claim 10 including a thin membrane disposed about at least one of said toroids to space said toroids apart and prevent premature mixing of said components.

12. The protective devices of claim 11 wherein said membrane comprises tin foil.

13. The protective devices of claim 11 wherein said membrane comprises a thermoplastic material.

14. The protective devices of claim 10 wherein said toroids are split so as to define air gaps therein and including a split ring of a flexible material disposed about and carrying said toroids, said ring defining an outer diameter substantially equal to the inner diameter of said casing proximate said end wall thereof whereby said ring and said toroids can be compressed and slidably disposed within said casing to a position adjacent said end wall thereof, whereupon the outward flexure of said ring against the interior of said casing will maintain said ring and said toroids in place within said casing.

15. The protective devices of claim 7 wherein said expandable means includes a split ring of a flexible material and said components define a plurality of cylindrical members carried by and within said ring with each of said cylindrical members of one component being disposed between a pair of cylindrical members of the other component and wherein said ring can be compressed and with said cylindrical members, slidably disposed within said casing to a position adjacent said end wall thereof, whereupon the outward flexure of said ring against the interior of said casing will maintain said ring and said cylindrical members in place within said casing.

16. The protective devices of claim 15 including one or more thin protective membranes disposed about and between said cylindrical members for prolonging the shelf life of said components comprising said cylindrical members.

17. The protective devices of claim 16 wherein said membranes comprise tin foil.

18. The protective devices of claim 16 wherein said membranes comprise a thermal plastic material.

19. The protective devices of claim 7 wherein said expandable means includes a cup member defining an inner wall portion, an outer wall portion and a plurality of adjacent collapsible cells disposed between said inner and outer wall portions, said two components being alternately deposited within said cells.

20. The protective devices of claim 19 including a sealing means disposed about said cells for maintaining said component therein during and prior to the ejection of fluid from the syringe.

21. A protective device for use with a hypodermic syringe for preventing accidental needle sticks after fluid has been ejected from the syringe, said device comprising:
a hollow, cylindrical casing defining a forward end wall having an opening therein, a rearward open end, and an annular gripping flange adjacent said rearward end, said casing being adapted to be disposed about a syringe such that the syringe is reciprocally translatable therein, the syringe needle projects through said opening in said forward end wall and said gripping flange is axially spaced from the syringe flange;
a two-component expandable foaming means disposed in the casing adjacent said end wall thereof, the two components of said means being maintained in a spaced relationship within said casing and upon being compressed together, mix and react to form an expanding and hardening foam; and
means carried by said casing for spacing said expanding foaming means from the syringe upon said casing being disposed about the syringe, said means being adapted to maintain said spacing during ejection of fluid from the syringe and collapse upon the application of additional force being exerted upon the syringe subsequent to such ejection, whereby said components are compressed together by the syringe, causing said components to mix and react, such that the expanding foam will force the syringe rearwardly within said casing and harden about the syringe needle so as to encapsulate the needle within the hardened foam within said casing.

22. The protective device of claim 21 wherein said spacing means comprises a plurality of collapsible tab members projecting rearwardly from said angular gripping flange and abutting the syringe flange upon said casing being disposed about the syringe.

23. The protective devices of claims 21 or 22 wherein one of said two components is comprised of isocyanate and the other of said components is comprised of polyol.

24. The protective devices of claims 21 or 22 including a thin membrane disposed about at least one of said components to space said components apart and prevent premature mixing thereof.

25. The protective devices of claims 21 or 22 wherein said components are carried by and disposed within a split ring of flexible material, said ring defining an outer diameter substantially equal to the inner diameter of said casing proximate to said end wall thereof and whereby said ring can be compressed and with said components carried thereby and slidably disposed within said casing to a position proximate said end wall thereof, whereupon the outward flexure of said ring against the interior of said casing will maintain said ring and said component in place within said casing.

26. The protective devices of claims 21 and 22 including a cup member defining an inner wall portion, an outer wall portion and a plurality of adjacent collapsible cells disposed between said inner and outer wall portions, said two components being alternately deposited within said cells.

27. The protective device of claim 3 wherein said collapsible means comprises a plurality of collapsible tab members projecting rearwardly from said angular gripping flange and abutting the syringe flange upon said casing being disposed about the syringe.

28. A protective device for use with a hypodermic syringe for preventing accidental needle sticks after fluid has been ejected from the syringe, said device comprising:
a hollow cylindrical casing defining a forward end wall having an opening therein, a rearward open end and an annular gripping flange adjacent said rearward end, said casing being adapted to be disposed about a syringe such that the syringe is reciprocally translatable therein, the syringe needle projects through said opening in said forward end wall and said gripping flange is axially spaced from the syringe flange;
expandable means disposed in said casing, said means being activated to an expanded state upon being compressed within said casing by the syringe; and
collapsible means carried by said casing and being adapted to abut the syringe upon said casing being disposed about the syringe to prevent the syringe from compressing said expandable means prior to and during ejection of fluid from the syringe and collapsing upon the application of additional force being exerted upon the syringe subsequent to such ejection, allowing the syringe to compress and activate said expandable means, whereupon said expandable means expands within said casing adjacent the forward end wall thereof to force the syringe rearwardly within said casing and draw the syringe needle into said casing.

29. A protective device for use with a hypodermic syringe for preventing accidental needle sticks after fluid has been ejected from the syringe, said device comprising:
a hollow cylindrical casing defining a forward end wall having an opening therein, a rearward open end and an annular gripping flange adjacent said rearward end, said casing being adapted to be disposed about a syringe such that the syringe is reciprocally translatable therein, the syringe needle projects through said opening in said forward end wall and said gripping flange is axially spaced from the syringe flange;
expandable means disposed in said casing in a non-expanded state proximate said forward end wall thereof and adapted to be activated to an expanded state upon said casing being disposed about the syringe to force the syringe rearwardly within said casing and draw the needle into said casing; and
means disposed within said casing enclosing said expandable means for maintaining said expandable means in a non-expanded state prior to and during ejection of fluid from the syringe, said means being adapted to collapse upon the application of additional force being asserted upon the syringe subsequent to such ejection, whereupon said expandable means expands within said casing.

30. A hypodermic syringe needle containment assembly for preventing accidental needle sticks after fluid has been ejected from the syringe, said assembly comprising:
- a hypodermic syringe having a barrel portion, a gripping flange proximate one end of said barrel portion and a needle projecting from the other end of said barrel portion;
- a hollow cylindrical casing defining a forward end wall having an opening therein, a rearward open end and an annular gripping flange adjacent said rearward end, said casing being adapted to be disposed about said barrel portion of said syringe such that the syringe is reciprocally translatable therein, said needle projects through said opening in said forward end wall and said gripping flange is axially spaced from the gripping flange on said syringe barrel;
- expandable means disposed in said casing adjacent said forward end wall thereof, said means being activated to an expanded state upon being compressed by the syringe between the syringe and said forward end wall of said casing; and
- collapsible means carried by said casing and abutting a portion of said syringe upon said casing being disposed about said syringe, preventing said syringe from compressing said expandable means prior to and during ejection of fluid from said syringe and collapsing upon the application of addition force being exerted upon said syringe subsequent to such ejection, allowing said syringe to compress and activate said expandable means, whereby said expandable means expands within said casing between the forward end wall thereof and said syringe, forcing said syringe rearwardly within said casing and drawing the syringe needle into said casing.

31. The assembly of claim 30 wherein said collapsible means comprises a plurality of collapsible tab members projecting rearwardly from said annular gripping flange on said casing and abutting the syringe flange upon said casing being disposed about said syringe.

32. The assembly to claims 30 or 31 wherein said expandable means comprises a two component forming means, the two components of said means being spaced apart within said casing, and upon being compressed by said syringe within said casing upon the collapse of said collapsible means, mix together and react to form an expanding foam, said foam forcing said syringe rearwardly within said casing and harding about the syringe needle therein, thereby encapsulating the needle within the hardened foam in said casing.

* * * * *